United States Patent [19]

Barone et al.

[11] Patent Number: 5,405,863

[45] Date of Patent: Apr. 11, 1995

[54] ANTIOXIDANT CARDIOPROTECTIVE USE OF, AND METHOD OF TREATMENT USING, HYDROXYCARBAZOLE COMPOUNDS

[75] Inventors: Frank C. Barone, Audubon; Giora Feuerstein, Wynnewood; Tian-Li Yue, Havertown, all of Pa.

[73] Assignee: SmithKline Beecham Corporation, Philadelphia, Pa.

[21] Appl. No.: 128,327

[22] Filed: Sep. 28, 1993

Related U.S. Application Data

[63] Continuation of Ser. No. 983,916, Dec. 1, 1992, abandoned.

[51] Int. Cl.$^6$ .............................................. A61K 31/40
[52] U.S. Cl. ................................................... 514/411
[58] Field of Search ........................................ 514/411

[56] References Cited

U.S. PATENT DOCUMENTS 4,503,067  3/1985  Wiedemann et al. ............... 514/411

OTHER PUBLICATIONS

Lysko et al., *Chemical Abstracts* 118(7):52140v, Jun. 1992.
Hoeher et al., *Chemcial Abstracts* 111(23):208919z, Apr. 1989.
Hamburger et al., *Chemical Abstracts* 115(19):198096v, Mar. 1991.
Hashimoto et al., *Chemical Abstracts* 116(1) 469y, Mar. 1991.

*Primary Examiner*—Raymond Henley, III
*Assistant Examiner*—William R. A. Jarvis
*Attorney, Agent, or Firm*—Yuriy P. Stercho; Stuart R. Suter; Edward T. Lentz

[57] ABSTRACT

This invention relates to a new antioxidant use of, and method of treatment using certain hydroxycarbazole compounds or a pharmaceutically acceptable salt thereof. More specifically, the compounds are useful for the prevention of oxidative tissue damage to organs, particularly the central nervous system including the brain, in mammals afflicted with disease-induced ischemic trauma, particularly stroke.

11 Claims, No Drawings

ANTIOXIDANT CARDIOPROTECTIVE USE OF, AND METHOD OF TREATMENT USING, HYDROXYCARBAZOLE COMPOUNDS

This is a continuation of application Ser. No. 07/983,916, Dec. 1, 1992, now abandoned.

FIELD OF THE INVENTION

The present invention relates to a new medical use of, and method of treatment using, the hydroxycarbazole compounds of Formula I, as oxygen radical scavengers, or antioxidants, for protection of vital organs, particularly the cardiovascular system including the heart, from oxidative damage. In particular, the present invention provides a new use for such hydroxycarbazole compounds for making pharmaceutical compositions useful in prevention of organ reperfusion injury including related acute inflammation, particularly cardioprotection, that is, protection of the cardiovascular system from traumatic and post-traumatic injury associated with myocardial infarction.

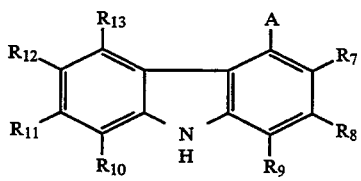

(I)

wherein:
$R_7$–$R_{13}$ are independently —H or —OH; and
A= is independently H, —OH, or a moiety of Formula II:

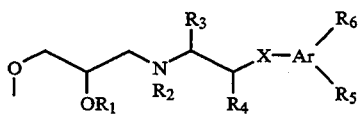

(II)

wherein:
$R_1$ is hydrogen, lower alkanoyl of up to 6 carbon atoms or aroyl selected from benzoyl and naphthoyl;
$R_2$ is hydrogen, lower alkyl of up to 6 carbon atoms or arylalkyl selected from benzyl, phenylethyl and phenylpropyl;
$R_3$ is hydrogen or lower alkyl of up to 6 carbon atoms;
$R_4$ is hydrogen or lower alkyl of up to 6 carbon atoms, or when X is oxygen, $R_4$ together with $R_5$ can represent —$CH_2$—O—;
X is a valency bond, —$CH_2$, oxygen or sulfur;
Ar is selected from phenyl, naphthyl, indanyl and tetrahydronaphthyl;
$R_5$ and $R_6$ are individually selected from hydrogen, fluorine, chlorine, bromine, hydroxyl, lower alkyl of up to 6 carbon atoms, a —$CONH_2$— group, lower alkoxy of up to 6 carbon atoms, benzyloxy, lower alkylthio of up to 6 carbon atoms, lower alkysulphinyl of up to 6 carbon atoms and lower alkylsulphonyl of up to 6 carbon atoms; or
$R_5$ and $R_6$ together represent methylenedioxy;
and pharmaceutically acceptable salts thereof.

BACKGROUND OF THE INVENTION

Morbidity and mortality associated with disease-induced ischemic trauma of the vital organs, for instance as seen in acute myocardial infarction, represent major health problems in the developed world.

Considerable biochemical, physiological and pharmacological evidence supports the occurrence and importance of oxygen free radical-induced lipid peroxidation (LPO) in cardiac ischemia/reperfusion injury (Meerson, F. Z. et al., *Basic Res. Cardiol.* (1982) 77, 465–485; Downey, J. M., *Ann. Rev. Physiol.* (1990) 52, 487–504). It has been proposed that reoxygenation of ischaemic myocardium leads to generation of $O_2$ and $H_2O_2$ within the tissue which can, in the presence of transition metal ions, become converted into highly-reactive hydroxyl radicals (OH) which initiate LPO, a radical chain reaction, leading to changes in cell membrane integrity and tissue injury (McCord, J. M., *N. Engl. J. Med.* (1985), 312, 159–163; McCord, J. M., *Fed. Proc.*, (1987) 46, 2402; Kagan, V. E., *Lipid Peroxidation in Biomembranes*, (1988) CRC Press, Boca Raton Fla.). Marked activation of LPO in experimental myocardial infarction, as well as reoxygenation following transitory ischemia, have been demonstrated (Meerson et al., 1982; Rao et al., *Adv. Exp. Med. Biol.*, (1983) 161,347–363). Exposure of myocytes or whole heart to oxidant-generating systems produced severe injury, including inactivation of the ATP-dependent $Ca^{++}$ sequestering system of cardiac sarcoplasmic reticulum (Halliwell, B. and Gutteridge, J. M. C. *Free Radicals in Biology and Medicine*, 2d ed., (1989) Clarendon Press, Oxford, England, 442–444). A significant increase in plasma LPO levels has also been reported recently in patients with myocardial infarction, especially during the initial 48 hrs after an attack (Loeper et al., *Clinica Chimica Acta*, (1991) 196, 119–126). The importance of LPO and oxygen radicals in tissue damage associated with ischemia is further supported by the protective effect of natural and synthetic antioxidants such as vitamin E and the lazaroid U-74500A (Levitt, M. A., *Clin. Res.* (1991) 39, 265A) or antioxidant enzymes such as superoxide dismutase (SOD) and catalase in diverse ischemic models (for review see Halliwell and Gutteridge, 1989).

Given the high incidence of disease-induced ischemic trauma of the vital organs, in particular, of the cardiovascular system including the heart, e.g., together with the high survival rate of patients suffering these traumas in the developed world, there is a great need for pharmaceutical agents which prevent the occurence of such traumas as well as which protect the vital organs of patients in post-traumatic recovery from organ ischemic reperfusion injury.

SUMMARY OF THE INVENTION

In a first aspect, the present invention provides a new medical use for the hydroxycarbazole compounds of Formula I as oxygen radical scavengers or antioxidants for protection of vital organs from oxidative damage. In particular, the present invention provides a new use for compounds preferably selected from the group consisting essentially of the compounds of Formula I wherein A is the moiety of Formula II wherein R1 is —H, R2 is —H, R3 is OH, R4 is —H, X is O, Ar is phenyl, R5 is ortho —OH, and R6 is —H, and one of $R_7$, $R_9$, or $R_{10}$ is —OH, most preferably the compound of Formula I wherein A is the moiety of Formula II wherein R1 is —H, R2 is —H, R3 is —H, R4 is —H, X is O, Ar is phenyl, R5 is ortho —OH, and R6 is —H, and R7 is —OH, or a pharmaceutically acceptable salt thereof, said compounds being used to make pharmaceutical compositions useful in the prevention of organ reperfusion injury, including related acute inflammation generally, and particularly useful in cardioprotection, that is, protection of the cardiovascular system from traumatic and post-traumatic injury associated with myocardial infarction, in particular, prevention of extensive myocardial infarction and reduction of the area of infarcted myocardial tissue following coronary thrombosis.

In a second aspect, the present invention also provides a method of treatment for prevention of oxidative tissue damage to organs afflicted with disease-induced ischemic trauma, particularly cardioprotection, that is, prevention of stroke and reduction of morbidity resulting from myocardial infarction, in mammals comprising internally administering to a mammal, preferably a human, in need thereof an effective amount of a compound selected from the group consisting essentially of the compounds of Formula I, preferably selected from the group consisting essentially of the compounds of Formula I wherein A is the moiety of Formula II wherein $R_1$ is —H, $R_2$ is OH, $R_3$ is —H, $R_4$ is —H, X is O, Ar is phenyl, $R_5$ is ortho —OH, and $R_6$ is —H, and one of $R_7$, $R_9$, or $R_{10}$ is —OH, most preferably the compound of Formula I wherein A is the moiety of Formula II wherein $R_1$ is —H, $R_2$ is —H, $R_3$ is —H, $R_4$ is —H, X is O, Ar is phenyl, $R_5$ is ortho —OH, and $R_6$ is —H, and $R_7$ is —OH, or a pharmaceutically acceptable salt thereof.

DETAILED DESCRIPTION OF THE INVENTION

U.S. Pat. No. 4,503,067 discloses carbazolyl-(4)-oxy-propanolamine compounds of Formula III:

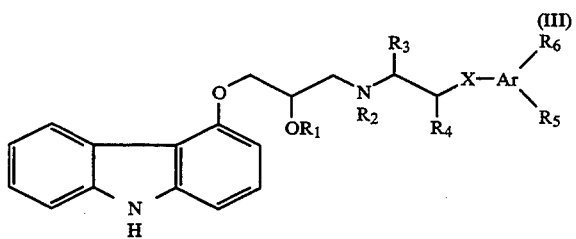

(III)

wherein:

$R_1$ is hydrogen, lower alkanoyl of up to 6 carbon atoms or aroyl selected from benzoyl and naphthoyl;

$R_2$ is hydrogen, lower alkyl of up to 6 carbon atoms or arylalkyl selected from benzyl, phenylethyl and phenylpropyl;

$R_3$ is hydrogen or lower alkyl of up to 6 carbon atoms;

$R_4$ is hydrogen or lower alkyl of up to 6 carbon atoms, or when X is oxygen, $R_4$ together with $R_5$ can represent —CH$_2$—O—;

X is a valency bond, —CH$_2$, oxygen or sulfur;

Ar is selected from phenyl, naphthyl, indanyl and tetrahydronaphthyl;

$R_5$ and $R_6$ are individually selected from hydrogen, fluorine, chlorine, bromine, hydroxyl, lower alkyl of up to 6 carbon atoms, a —CONH$_2$— group, lower alkoxy of up to 6 carbon atoms, benzyloxy, lower alkylthio of up to 6 carbon atoms, lower alkysulphinyl of up to 6 carbon atoms and lower alkylsulphonyl of up to 6 carbon atoms; or $R_5$ and $R_6$ together represent methylenedioxy;

and pharmaceutically acceptable salts thereof.

This patent further discloses a compound of Formula III, better known as carvedilol (1-(carbazol-4-yloxy-3-[[2-(o-methoxyphenoxy)ethyl]amino]-2-propanol), having the structure shown in Formula IV:

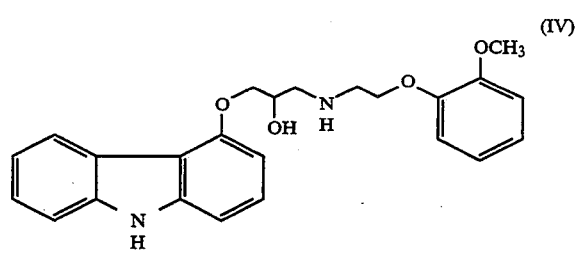

(IV)

These compounds, of which carvedilol is exemplary, are novel multiple action drugs useful in the treatment of mild to moderate hypertension and having utility in angina and congestive heart failure (CHF). Carvedilol is known to be both a competitive β-adrenoceptor antagonist and a vasodilator, and is also a calcium channel antagonist at higher concentrations. The vasodilatory actions of carvedilol result primarily from $α_1$-adrenoceptor blockade, whereas the β-adrenoceptor blocking activity of the drug prevents reflex tachycardia when used in the treatment of hypertension. These multiple actions of carvedilol are responsible for the antihypertensive efficacy of the drug in animals, particularly in humans, as well as for utility in the treatment of angina and CHF.

During ischemic organ trauma, as in acute myocardial infarction, a high proportion of ischemic organ cells become irreversibly damaged and necrotic, the extent of injury being dependent upon the length of time that the trauma, e.g. the arterial occlusion, persists. The protection of myocardial cells from such damage and necrosis during occlusion occurring during myocardial infarction and post-infarction reperfusion is essential to achieving the therapeutic goal of restoration of cardiac function; here and throughout this application this property is referred to by the term "cardioprotection" and its synonyms.

While traditional β-adrenoceptor antagonists, for instance propranolol, have a significant cardioprotective effect, they also often have undesireable side effects such as bradycardia, elevated disatolic blood pressure and total peripheral resistance cardiodepression. However, carbazolyl-(4)-oxypropanolamine compounds of Formula III, particularly carvedilol, are effective cardioprotective agents at antihypertensive doses which unexpectedly minimize these consequences. At antihypertensive doses the combination of β-adrenoceptor blocking and vasodilatory properties of carvedilol provides cardioprotection during and after acute myocardial infarction. It is believed that the cardioprotective effects of β-adrenoceptor antagonists at such dosages result from an improvement in the balance between myocardial oxygen supply and demand by reducing myocardial work, which occurs secondary to reductions in both heart rate and contractility.

Some of the compounds of Formula I are known to be metabolites of carvedilol in human and other mammalian (e.g. gerbil) systems. The preferred compounds of the present invention, that is, the compounds of Formula I wherein A is the moiety of Formula II wherein R1 is —H, R2 is —H, R3 is —H, R4 is —H, X is O, Ar is phenyl, R5 is ortho —OH, and R6 is —H, and one of $R_7$, $R_9$, or $R_{10}$ is —OH are known to be metabolites of carvedilol.

We have recently discovered, by use of electron paramagnetic resonance (EPR) studies, that the hydroxycarbazole compounds of Formula I are oxygen radical scavengers. We have also discovered that, as oxygen scavengers, the above-described compounds act to inhibit LPO, and further that the hydroxycarbazole compounds of Formula I are surprisingly effective protective agents in generally preventing a wide variety of disease states associated with oxidative tissue damage to the organs due to LPO following ischemic traumas. In particular, the compounds of the present invention are especially useful in cardioprotection, that is, prevention of acute myocardial infarction, and reduction of morbidity resulting from the sequelae of myocardial infarction and reperfusion.

As is further illustrated below, the compounds of Formula I, preferably selected from the group consisting essentially of the compounds of Formula I wherein A is the moiety of Formula II wherein R1 is —H, R2 is —H, R3 is —H, R4 is —H, X is O, Ar is phenyl, R5 is ortho —OH, and R6 is —H, and one of $R_7$, $R_9$, or $R_{10}$ is —OH, most preferably the compound of Formula I wherein A is the moiety of Formula II wherein R1 is —H, R2 is —H, R3 is —H, R4 is —H, X is O, Ar is phenyl, R5 is ortho —OH, and R6 is —H, and $R_7$ is —OH, exhibit cardioprotection, and are especially useful for providing a beneficial cardioprotective effect by prevention of oxidative tissue damage in ischemic human myocardium; thus these compounds have utility as adjunctive therapy following myocardial infarction. Chronic administration of these compounds can both reduce the risk of acute myocardial infarction in individuals at risk thereof as well as provide adjunctive therapy by reducing the magnitude of oxidative tissue damage following an ischemic cardiac event. Because hypertensive individuals are at increased risk of stroke, the cardioprotective use of the present compounds at appropriate dosing regimens in combination with antihypertensive therapy significantly reduces the risk of acute myocardial infarction, reinfarction, the area of infarcted tissue should reinfarction occur, and sudden cardiac death in such patients.

The compounds of Formula I, preferably those selected from the group consisting essentially of the compounds of Formula I wherein A is the moiety of Formula II wherein R1 is —H, R2 is —H, R3 is —H, R4 is —H, X is O, Ar is phenyl, R5 is ortho —OH, and R6 is —H, and one of $R_7$, $R_9$, or $R_{10}$ is —OH, most preferably the compound of Formula I wherein A is the moiety of Formula II wherein R1 is —H, R2 is —H, R3 is OH, R4 is —H, X is O, Ar is phenyl, R5 is ortho —OH, and R6 is —H, and $R_7$ is —OH, are useful for cardioprotection in humans according to the present invention at dosages ranging from about 1-3 mg/kg i.v.b.i.d. and 3-30 mg/kg p.o. b.i.d.

The present invention also provides a method of treatment for prevention of oxidative tissue damage to organs afflicted with disease-induced ischemic trauma in mammals comprising internally administering to a mammal, preferably a human, in need thereof an effective amount of a compound selected from the group consisting essentially of the compounds of Formula I, preferably those selected from the group consisting essentially of the compounds of Formula I wherein A is the moiety of Formula II, and one of $R_7$, $R_9$, or $R_{10}$ is —OH, most preferably the compound of Formula I wherein A is the the moiety of Formula II, and $R_7$ is —OH, or a pharmaceutically acceptable salt thereof.

Compounds of Formula I may be conveniently prepared as described by way of example in Example 1.

Pharmaceutical compositions of the compounds of Formulae I for cardioprotective use according to the present invention, may be formulated as solutions or lyophilized powders for parenteral administration. Powders may be reconstituted by addition of a suitable diluent or other pharmaceutically acceptable carrier prior to use. The liquid formulation is generally a buffered, isotonic, aqueous solution. Examples of suitable diluents are normal isotonic saline solution, standard 5% dextrose in water or buffered sodium or ammonium acetate solution. Such formulation is especially suitable for parenteral administration, but may also be used for oral administration or contained in a metered dose inhaler or nebulizer for insufflation. It may be desirable to add excipients such as ethanol, polyvinylpyrrolidone, gelatin, hydroxy cellulose, acacia, polyethylene glycol, mannitol, sodium chloride or sodium citrate.

Alternatively, these compounds may be encapsulated, tableted or prepared in a emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, ethanol, and water. Solid carriers include starch, lactose, calcium sulfate dihydrate, terra alba, magnesium stearate or stearic acid, talc, pectin, acacia, agar or gelatin. The carrier may also include a sustained release material such as glyceryl monostearate or glyceryl distearate; alone or with a wax. The amount of solid carrier varies but, preferably, will be between about 20 mg to about 1 g per dosage unit. The pharmaceutical preparations are made following the conventional techniques of pharmacy involving milling, mixing, granulating, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

The following Example is purely illustrative and is provided to teach how to make the compounds of the present invention, but is not intended to limit the scope of the present invention in any manner.

In the Example, all temperatures are in degrees Centigrade (°C.).

EXAMPLES

EXAMPLE 1

The compound of Formula I wherein $R_7$ is —OH, and R8–R13 are all —H, and A is the moiety of Formula II wherein R1 is —H, R2 is —H, R3 is —H, R4 is —H, X is I, Ar is phenyl, R5 is ortho —OH, and R6 is —H was synthesized as follows and is exemplary of the synthetic route to the compounds of Formula I.

3-Benzyloxy-4-hydroxycarbazole

Benzoyl peroxide (881 mg, 2.73 mmol) was added in one portion to a suspension of 4-hydroxycarbazole (500 mg, 2.73 mmol) in 20 mL ChCl₃ at 25 C. The mixture was stirred for 2 h, then washed with water. The organic layer was dried over sodium sulfate and concentrated. Flash chromatography of the residue (silica, methylene chloride) provided 15 mg of 3-benzyloxy-4-hydroxycarbazole. MS (DCI/NH₃): 304.2 (M+H)+.

Subsequent steps to yield the product are well-known: reaction with epichlorohydrin, then 2-methoxyphenethylamine, and finally saponification of the benzoyl ester.

The above description fully discloses how to make and use the present invention. However, the present invention is not limited to the particular embodiment described hereinabove, but includes all modifications thereof within the scope of the following claims.

We claim:

1. A method of treatment for prevention of oxidative tissue damage to organs afflicted with disease-induced ischemic trauma in mammals comprising internally administering to a mammal in need thereof an effective amount of a compound selected from the group consisting essentially of the compounds of Formula I:

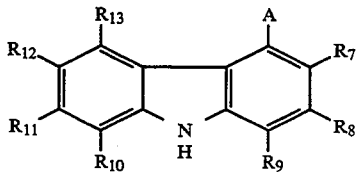

wherein:
$R_7$–$R_{13}$ are independently —H or —OH, provided that at least one of $R_7$–$R_{12}$ is —OH; and
A= is independently H, —OH, or a moiety of Formula II:

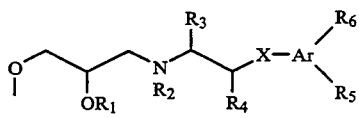

wherein:
$R_1$ is hydrogen, lower alkanoyl of up to 6 carbon atoms or aroyl selected from benzoyl and naphthoyl;
$R_2$ is hydrogen, lower alkyl of up to 6 carbon atoms or arylalkyl selected from benzyl, phenylethyl and phenylpropyl;
$R_3$ is hydrogen or lower alkyl of up to 6 carbon atoms;
$R_4$ is hydrogen or lower alkyl of up to 6 carbon atoms, or when X is oxygen, $R_4$ together with $R_5$ can represent —CH₂—O—;
X is a valency bond, —CH₂, oxygen or sulfur;
Ar is selected from phenyl, naphthyl, indanyl and tetrahydronaphthyl;
$R_5$ and $R_6$ are individually selected from hydrogen, fluorine, chlorine, bromine, hydroxyl, lower alkyl of up to 6 carbon atoms, a —CONH₂— group, lower alkoxy of up to 6 carbon atoms, benzyloxy, lower alkylthio of up to 6 carbon atoms, lower alkysulphinyl of up to 6 carbon atoms and lower alkylsulphonyl of up to 6 carbon atoms; or
$R_5$ and $R_6$ together represent methylenedioxy;
and pharmaceutically acceptable salts thereof.

2. A method of treatment according to claim 1 wherein said mammal is human.

3. A method of treatment according to claim 1 wherein said compound is a compound of Formula I wherein:
A is the moiety of Formula II wherein wherein $R_1$ is —H, $R_2$ is —H, $R_3$ is —H, $R_4$ is —H, X is O, Ar is phenyl, $R_5$ is ortho —OH, and $R_6$ is —H; and one of $R_7$, $R_9$, or $R_{10}$ is —OH.

4. A method of treatment according to claim 3 wherein said compound is a compound of Formula I wherein:
A is the moiety of Formula II wherein wherein $R_1$ is —H, $R_2$ is —H, $R_3$ is —H, $R_4$ is —H, X is O, Ar is phenyl, $R_5$ is ortho —OH, and $R_6$ is —H; and $R_7$ is —OH.

5. A method of treatment for prevention of tissue damage to cardiovascular organs afflicted with disease-induced ischemic trauma in mammals comprising internally administering to a mammal in need thereof an effective amount of a compound selected from the group consisting essentially of compounds of Formula I:

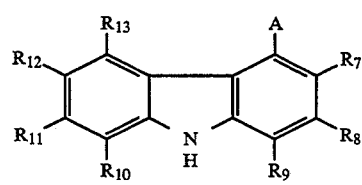

wherein:
$R_7$–$R_{13}$ are independently —H or —OH, provided that at least one of $R_2$–$R_{13}$ is —OH; and
A= is independently H, —OH, or a moiety of Formula II:

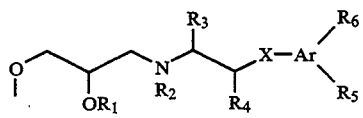

wherein:
$R_1$ is hydrogen, lower alkanoyl of up to 6 carbon atoms or aroyl selected from benzoyl and naphthoyl;
$R_2$ is hydrogen, lower alkyl of up to 6 carbon atoms or arylalkyl selected from benzyl, phenylethyl and phenylpropyl;
$R_3$ is hydrogen or lower alkyl of up to 6 carbon atoms;
$R_4$ is hydrogen or lower alkyl of up to 6 carbon atoms, or when X is oxygen, $R_4$ together with $R_5$ can represent —CH₂—O—;
X is a valency bond, —CH₂, oxygen or sulfur;
Ar is selected from phenyl, naphthyl, indanyl and tetrahydronaphthyl;
$R_5$ and $R_6$ are individually selected from hydrogen, fluorine, chlorine, bromine, hydroxyl, lower alkyl of up to 6 carbon atoms, a —CONH₂— group, lower alkoxy of up to 6 carbon atoms, benzyloxy, lower alkylthio of up to 6 carbon atoms, lower alkysulphinyl of up to 6 carbon atoms and lower alkylsulphonyl of up to 6 carbon atoms; or
$R_5$ and $R_6$ together represent methylenedioxy;
and pharmaceutically acceptable salts thereof.

6. A method of treatment according to claim 5 wherein said mammal is human.

7. A method of treatment according to claim 5 wherein said compound is a compound of Formula I wherein:
A is the moiety of Formula II wherein wherein $R_1$ is —H, $R_2$ is —H, $R_3$ is —H, $R_4$ is —H, X is O, Ar is phenyl, $R_5$ is ortho —OH, and $R_6$ is —H; and one of $R_7$, $R_9$, or $R_{10}$ is —OH.

8. A method of treatment according to claim 7 wherein said compound is a compound of Formula I wherein:
A is the moiety of Formula II wherein wherein $R_1$ is —H, $R_2$ is —H, $R_3$ is —H, $R_4$ is —H, X is O, Ar is phenyl, $R_5$ is ortho —OH, and $R_6$ is —H; and $R_7$ is —OH.

9. A method of treatment for prevention of tissue damage to cardiovascular organs afflicted with disease-induced ischemic trauma of human patients surviving an acute myocardial infarction, comprising internally administering to a patient in need thereof an effective dose of a pharmaceutical composition comprising a compound according to claim 1, said treatment reducing the risk of oxidative damage to myocardial tissue.

10. A method of treatment according to claim 1 wherein said compound is in the form of a pharmaceutical composition is suitable for parenteral administration.

11. A method of treatment for the prevention of tissue damage to cardiovascular organs afflicted with disease-induced ischemic trauma of hypertensive patients at risk for myocardial infarction, comprising internally administering to a human patient in need thereof an effective dose of a pharmaceutical composition comprising a compound according to claim 1.

* * * * *